United States Patent
Duce et al.

(10) Patent No.: US 7,197,912 B1
(45) Date of Patent: Apr. 3, 2007

(54) GAS SENSOR SEAL AND METHOD OF PRODUCING SAME

(75) Inventors: Richard W. Duce, Flushing, MI (US); Kathryn M. McCauley, Durand, MI (US); Richard C. Kuisell, Lapeer, MI (US)

(73) Assignee: Delphi Technologies, Inc., Troy, MI (US)

( * ) Notice: Subject to any disclaimer, the term of this patent is extended or adjusted under 35 U.S.C. 154(b) by 308 days.

(21) Appl. No.: 10/110,021

(22) PCT Filed: Oct. 26, 2000

(86) PCT No.: PCT/US00/41614

§ 371 (c)(1),
(2), (4) Date: Jul. 30, 2002

(87) PCT Pub. No.: WO01/35087

PCT Pub. Date: May 17, 2001

Related U.S. Application Data

(60) Provisional application No. 60/161,880, filed on Oct. 27, 1999.

(51) Int. Cl.
*G01N 27/12* (2006.01)
(52) U.S. Cl. ..................................... 73/31.05; 73/23.31
(58) Field of Classification Search ............... 73/31.05, 73/31.06, 23.31, 23.32; 204/424–429; 277/626, 277/615, 616, 617, 315
See application file for complete search history.

(56) References Cited

U.S. PATENT DOCUMENTS

| | | | | |
|---|---|---|---|---|
| 2,561,884 A | * | 7/1951 | Perrow | 277/616 |
| 3,680,894 A | * | 8/1972 | Young | 285/112 |
| 4,217,179 A | * | 8/1980 | Fray | 205/781.5 |
| 4,298,206 A | * | 11/1981 | Kojima | 277/626 |
| 5,238,551 A | * | 8/1993 | Katsu et al. | 204/426 |
| 5,329,806 A | * | 7/1994 | McClanahan et al. | 73/31.05 |
| 5,490,412 A | * | 2/1996 | Duce et al. | 73/23.31 |
| 5,766,789 A | | 6/1998 | James et al. | 429/44 |

(Continued)

FOREIGN PATENT DOCUMENTS

| EP | 0 811 840 A2 | | 12/1997 |
|---|---|---|---|
| WO | WO-99/19722 | * | 4/1999 |
| WO | WO 01/34951 A2 | | 5/2001 |

OTHER PUBLICATIONS

Notification of Transmittal of the International Search Report or the Declaration; International Application No. PCT/US00/41616; International Filing Date, Oct. 26, 2000; Date of Mailing, Jul. 3, 2001; Applicant's or agent's file reference, DP-301244 PCT; Applicant, Delphi Technologies, Inc. et al.; 4 pages.

Notification of Transmittal of the International Search Report or the Declaration; International Application No. PCT/US00/41614; International Filing Date, Oct. 26, 2000; Date of Mailing, Jul. 18, 2001; Applicant's or agent's file reference, DP-301500 PC; Applicant, Delphi Technologies, Inc.; 6 pages.

*Primary Examiner*—Michael Cygan
(74) *Attorney, Agent, or Firm*—Paul L. Marshall

(57) ABSTRACT

A gas sensor seal (40) comprising a body (122), an upper portion having a flange (124), and at least one channel (130). The flange (124) has an extension (131) that extends from the upper portion, a bend (129) which extends from the extension (131) along the body (122), and a protrusion (128) which extends from the bend (129) toward the body (122). The channel (130) extends through the body (122) from the upper portion to a lower surface (126). A method for using the gas sensor seal (40) within a sensor (10) is also provided.

21 Claims, 3 Drawing Sheets

U.S. PATENT DOCUMENTS

| | | |
|---|---|---|
| 5,817,920 A | 10/1998 | Kuisell et al. .............. 73/23.31 |
| 5,874,664 A * | 2/1999 | Watanabe et al. .......... 73/23.32 |
| 5,886,248 A | 3/1999 | Paulus et al. .............. 73/23.31 |
| 5,948,963 A | 9/1999 | Kato et al. .................... 73/23.2 |
| 6,168,168 B1 * | 1/2001 | Brown ........................ 277/637 |
| 6,227,033 B1 | 5/2001 | Kainz ........................ 73/23.32 |
| 6,315,880 B1 * | 11/2001 | Reidmeyer et al. ......... 204/424 |
| 6,382,198 B1 | 5/2002 | Smith et al. ................ 123/673 |
| 6,453,726 B1 | 9/2002 | Gutierrez et al. .......... 73/31.05 |
| 6,484,561 B2 | 11/2002 | Jackson et al. ............ 73/31.05 |
| 6,514,397 B2 | 2/2003 | LaBarge et al. ............. 204/424 |
| 6,544,467 B2 | 4/2003 | Symons et al. ............. 264/618 |
| 6,562,747 B2 | 5/2003 | Symons et al. ............. 501/103 |
| 6,579,435 B2 | 6/2003 | Wang et al. ................ 204/425 |
| 6,579,436 B2 | 6/2003 | Wang et al. ................ 204/425 |
| 6,585,872 B2 | 7/2003 | Donelon et al. ............ 204/424 |

* cited by examiner

GAS SENSOR SEAL AND METHOD OF PRODUCING SAME

CROSS REFERENCE TO RELATED APPLICATIONS

This case claims the benefit of the filing date of the provisional application U.S. Provisional Application Ser. No. 60/161,880 filed Oct. 27, 1999, which is hereby incorporated by reference in its entirety.

TECHNICAL FIELD

This invention relates to gas sensors, and, more particularly, to seals for use in gas sensors.

BACKGROUND OF THE INVENTION

Sensors, particularly oxygen sensors, are used in a variety of applications that require qualitative and quantitative analysis of gases. In automotive applications, the direct relationship between the oxygen concentration in the exhaust gas and the air-to-fuel ratio of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically comprises an ionically conductive solid electrolyte material, a porous electrode on the exterior surface of the electrolyte exposed to the exhaust gases with a porous protective overcoat, and an electrode on the interior surface of the sensor exposed to a known oxygen partial pressure. Sensors typically used in automotive applications use a yttria stabilized zirconia based electrochemical galvanic cell with platinum electrodes, which operate in potentiometric mode to detect the relative amounts of oxygen present in the exhaust of an automobile engine. When opposite surfaces of this galvanic cell are exposed to different oxygen partial pressures, an electromotive force is developed between the electrodes on the opposite surfaces of the zirconia wall, according to the Nernst equation:

$$E = \left(\frac{RT}{4F}\right) \ln\left(\frac{P_{O_2}^{ref}}{P_{O_2}}\right)$$

where:
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

Sensors are electrically connected to the vehicle electrical system through the sensor body and wiring harness assembly. At the junction of the sensor and the wiring harness assembly, a seal 106, surrounding the electrical cables, is installed into the retainer 102 of the sensor, as illustrated in prior art FIG. 1. Conventional seals can be comprised of either a one-piece design (seal 106) or be in two parts, a seal 106 and a boot 104, to prevent water and other contaminant intrusion into the sensor 100. Seals comprised of two parts are more effective at preventing contamination, but are more costly. Additionally, during operation of the sensor, volatile hydrocarbons, present in these conventional seals, tend to evaporate at high temperatures, causing the seals to shrink from the walls of the upper shield, or from the cables, allowing contaminants to enter into the sensor.

What is needed in the art is a one-piece seal that prevents fluids, gases and other environmental contaminants from entering the sensor.

BRIEF SUMMARY OF THE INVENTION

The deficiencies of the above-discussed prior art are overcome or alleviated by the seal, gas sensor, and method of producing the sensor.

The seal comprises: a body, an upper portion having a flange, and at least one channel that extends through the body from the upper portion to a lower surface. The flange has an extension that extends from the upper portion, a bend which extends from the extension along the body, and a protrusion which extends from the bend toward the body.

The gas sensor comprises: a sensing element, having a lower portion disposed within a subassembly, and an upper portion disposed within a wiring harness assembly comprising an upper shield disposed around a wiring harness. The sensor also comprises: a seal having a body disposed in a first portion of the upper shield, and a flange wherein an edge of the upper shield is disposed between at least a portion of the flange and the body.

The method for producing the gas sensor, comprises: disposing an upper portion of a sensing element within a wiring harness assembly comprising an upper shield disposed around a wiring harness, disposing a lower portion of the sensing element within a subassembly, disposing at least a portion of a body of a seal concentrically within the upper shield, extending a flange over an edge of the upper shield, and crimping the upper shield around the seal.

The above-described and other features and advantages of the present invention will be appreciated and understood by those skilled in the art from the following detailed description, drawings, and appended claims.

BRIEF DESCRIPTION OF THE DRAWINGS

The apparatus and method will now be described by way of example, with reference to the accompanying drawing, which is meant to be exemplary, not limiting.

DETAILED DESCRIPTION OF THE INVENTION

Figure 1:
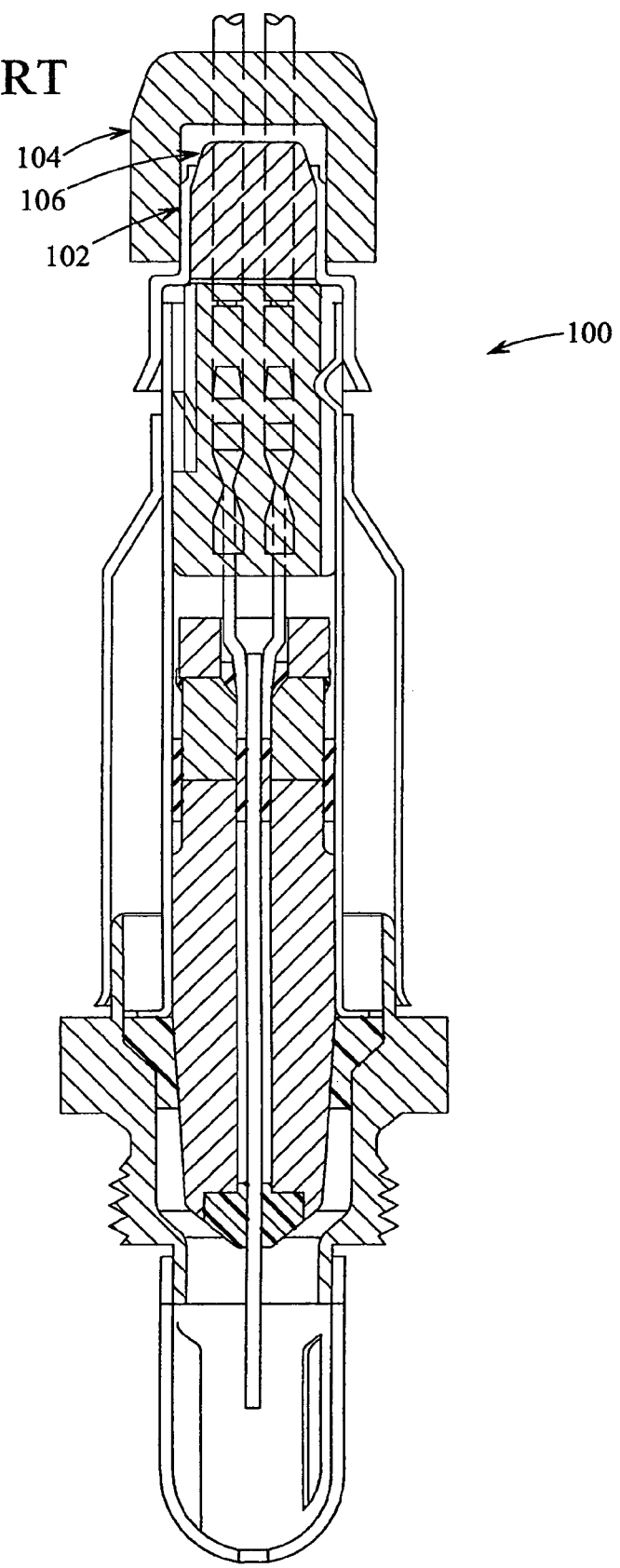
FIG. 1 is a cross-sectional view of a prior art gas sensor design.

Sensors are used in automobile engines to monitor the exhaust for the presence of different gases. The sensor typically comprises: a wiring harness assembly having an upper shield, a seal, electrical components (e.g., edge card connectors, male and/female terminals, spring clips or adaptors, and the like, as well as combinations comprising at least one of the foregoing components), and an upper portion of a sensing element; a subassembly having a shell, a lower shield, an optional internal shield, the lower portion of a sensing element, and optionally a high temperature mat material, a ceramic insulator or similar insulate, and a talc pack, and the like. The seal, located within the top portion of the upper shield, protects the sensor from the intrusion of water and other contaminants. The seal is a one-piece, multi-functional seal that protects the sensor from contamination and from shock loads or vibrations that may damage the sensing element, and retains the terminal support in place Referring now to FIG. 2, the exemplary oxygen sensor 10, having a wiring harness assembly 12 and a subassembly 14, is illustrated. The wiring harness assembly 12 generally includes the seal 40 and electrical components connected to the upper portion 84 of the sensing element 80 within the upper shield 20. The subassembly 14 generally includes the lower portion of the sensing element 80, an internal shield 35 in a lower shield 30, insulators 90, 92, talc pack 70, and a shell 50. Exemplary materials for the shields 20, 30, and 35 and for the shell 50 are stainless steels such as high chrome and/or high nickel stainless steels, and mixtures and alloys comprising at least one of the foregoing stainless steels, and the like, with all materials chosen for high temperature endurance, high-strength and corrosion resistance.

The lower shield 30 is securely coupled to the shell 50 such that a first end 82 of the sensing element 80 is disposed within the sensing chamber 31 to permit contact with and sensing of gas. The lower shield 30 defines the sensing chamber 31 and, disposed within the lower shield 30, is an internal shield 35 for receiving the sensing element 80. The lower shield 30 and the internal shield 35 incorporate a plurality of apertures 38, 39 for allowing passage of gas in and out of the sensing chamber 31 so that the gasses may be sensed by the receptive first end 82 of the sensing element 80.

Adjacent to the lower shield 30 and disposed between the shell 50 and sensing element 80 is at least a portion of the lower insulator 92. The lower insulator 92 comprises a high temperature material (i.e., a material capable of withstanding the "sensor operational conditions", e.g., exhaust gas temperatures up to about 1,000° C.), to provide insulation for the sensor 10. Some possible high temperature materials which are chosen for electrical insulation, thermal resistance, and mechanical support include ceramics and metals, among others, and combinations, alloys, and composites comprising at least one of the foregoing materials in the form of fibers (random, chopped, continuous, woven, and the like), woven and non-woven mesh, among others. The ceramic can include steatite, alumina, or the like, or combinations comprising at least one of the foregoing ceramics.

The lower insulator 92 is disposed within the shell 50. The shell 50 has a body portion 52 and a threaded portion 54. The body portion 52 is preferably shaped to accommodate a wrench or other tool for tightening the threaded portion 54 into a mount for an exhaust pipe or other component of an exhaust flow system, or wherever the gas sensor will be employed, thus enabling a sensor chamber 31 to be located within a flow of gasses to be measured. The shell 50 can be coupled to the upper shield 20 by a crimping or other process known in the art.

Optionally disposed on a lower portion of the shell 50 is a gasket 72, which provides a source of tension to help retain sensor 10 in operational position and serves as a seal against gas leakage. Another optional item that can be employed is a talc pack 70 which can be disposed within the shell 50 adjacent to the sensing element 80. The talc pack 70 can be disposed between the upper insulator 90 and the lower insulator 92 or between the shell shoulder 56 and the insulator 90, 92. The talc pack 70 holds the sensing element 80 in place by compacting talc powder around the sensing element 80. Alternatively, the talc pack 70 serves as a leak resistant seal that can be obtained by employing an inorganic material, such as talc, mica, kaolin, and the like, as well as combinations comprising at least one of the foregoing materials, between the sensing element 80 and lower shield 30.

Disposed within the shell 50 and the upper shield 20 can be the sensing element 80 having contact pads 86, 88. Portions of the sensing element 80 are disposed within the upper shield 20, the shell 50 and the lower shield 30. The sensing element 80 can be a planar or flat plate sensing element of a known type. At a first end 82 thereof, disposed in lower shield 30, the sensing element 80 includes a gas constituent-responsive structure (e.g., an electrochemical cell or the like) fabricated into the sensing element in a known manner, preferably along with a heater of a known type. Disposed at or near the second end 84 of the sensing element 80 are contact pads 86, 88, which are comprised of conventional materials known in the art.

Disposed at least partially within the upper shield 20 is the upper insulator 90 which typically extends into shell 50. This upper insulator can comprise any conventional design or the design set forth below. The upper insulator 90, which can be comprised of the same or similar types of high temperature materials as the lower insulator 92, insulates and protects the sensor 10. In one embodiment, the upper insulator 90, which can be a cylindrical device with a passage 93 of various widths for the insertion of the sensing element 80, optionally comprises an indentation or shelf 94 that extends outward from the passage 93 within the interior of the upper portion 91 to receive the terminal(s) 62, 63 of the wiring harness assembly 12. The terminal(s) 62, 63 are positioned such that they fit into, rest on or are supported by the upper insulator 90. By supporting the weight of the terminal(s) 62, 63 and the terminal support 60, the upper insulator 90 removes the weight and force from damaging the sensing element 80. This embodiment is further disclosed in Provisional Patent Application Ser. No. 60/161, 839, Attorney Docket No. DP-301500/DP-301244A (DEP-0133F), (that is hereby incorporated herein by reference in its entirety).

Terminal(s) 62, 63, which provide electrical communication between the sensing element 80 and the vehicle electrical system, can hold or retain the sensing element 80 in place by utilizing a spring design, as is known in the art. The terminal(s) 62, 63 are generally comprised of materials known in the art, which may include stainless steel, copper, brass, nickel, and the like, as well as combinations and alloys comprising at least one of the foregoing materials. Material and a terminal design which provides a substantial spring force under sensor operating conditions is preferred.

The terminals 62, 63 connect with the cable(s) or wire(s) 64, 65 entering the wiring harness assembly 12 from the vehicle electrical system. The cable(s) 64, 65 can be comprised of materials that are generally those that are known in the art, including copper, brass, stainless steel, nickel, and the like, as well as combinations and alloys comprising at least one of the foregoing materials. These cables are typically encased within an insulation, such as Teflon.

To support the terminal(s) 62, 63 and the sensing element 80, a terminal support 60 is provided. The terminal support 60 has a generally cylindrical shape optionally having a flat side, however, other designs are possible, such as multi-sided, and the like. Located within the top of the terminal support 60 are channels or holes for receiving terminals and electrical cables. Within the channels, an indentation or pocket can be created for receiving the terminals. The terminal support 60 may be formed of a material that is durable under sensor operation conditions. These materials, which should be chosen to provide for electrical insulation, thermal resistance, and mechanical support, can include thermoplastic; thermoset, ceramic, such as steatite, alumina, and the like; among others, and combinations comprising at least one of the foregoing terminal support materials, with ceramic and plastics often employed.

A one-piece, multifunctional fastener or seal 40 can comprise a body at least partially disposed within the upper end 22 of the upper shield 20, adjacent to the terminal support 60. The seal 40 is designed to have a lip, outcropping, or flange 124 and optional bumps, projections or protrusions 140. The seal 40, which can be made by conventional molding techniques known in the art, can comprise material capable of withstanding temperatures commensurate with the operation of an engine. Typical materials include fluoroelastomer, silicone, rubber, perfluoroelastomer, as well as other conventional seal materials and combinations comprising at least one of the foregoing materials.

Figure 3:
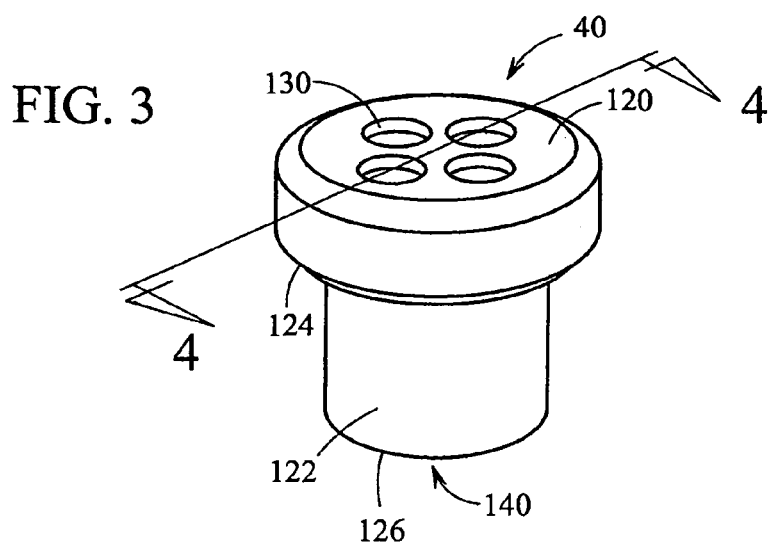
FIG. 3 is an isometric view of an exemplary seal.

This seal 40 protects the sensing element 80 by preventing the intrusion of water or other contaminants into the sensor 10. Referring to FIG. 3, the seal 40 is a one-piece unit having an upper portion 120 and a lower portion 122. The upper portion 120 has a flange 124 for receiving the upper shield. Located in the upper portion 120 are channels or holes 130 for receiving electrical cables (not shown). Located on the bottom 126 of the seal 40, are optional projections 140.

Figure 2:
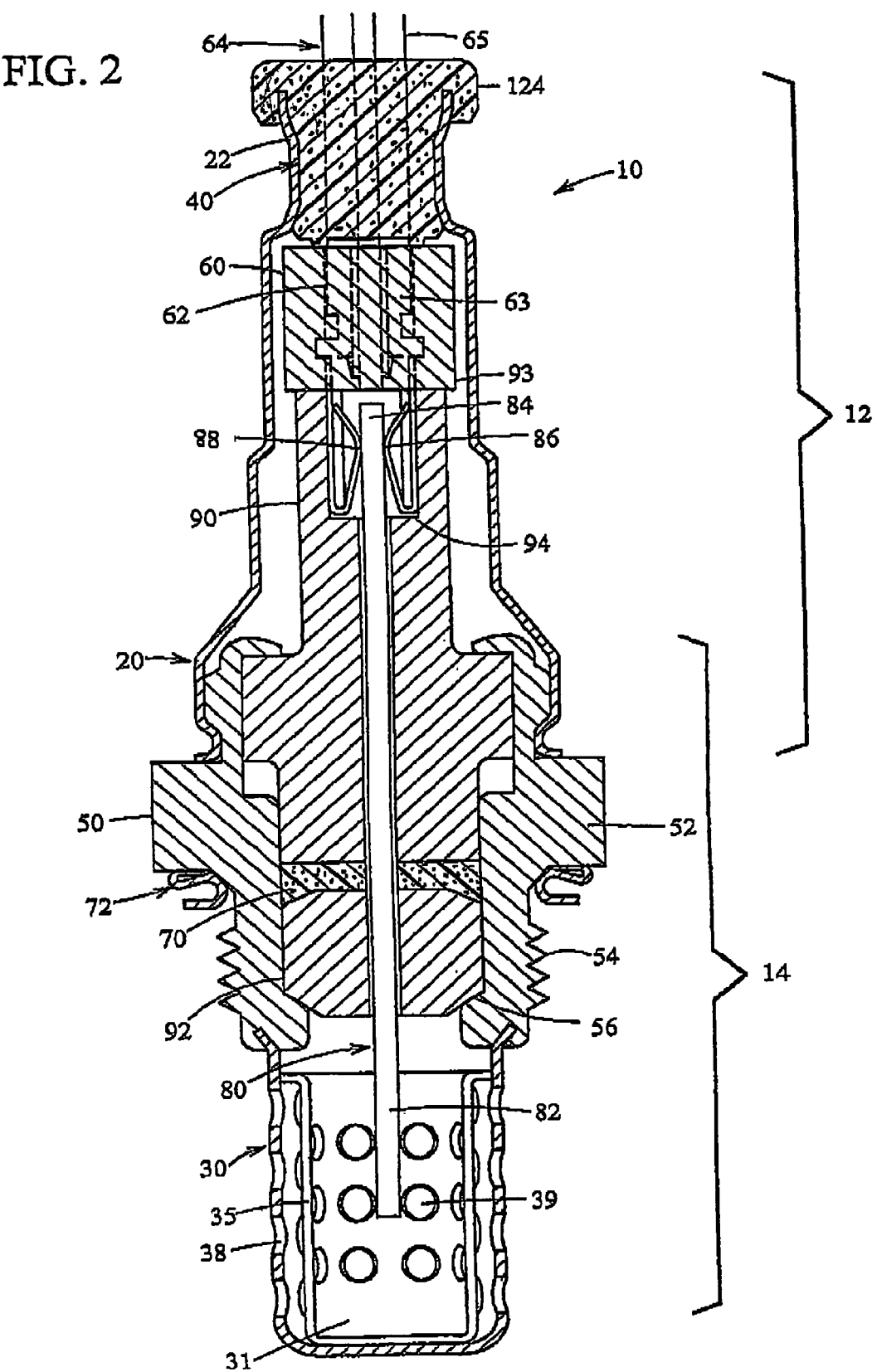
FIG. 2 is a cross-sectional view of a gas sensor design in accordance with the present invention.
Figure 4:
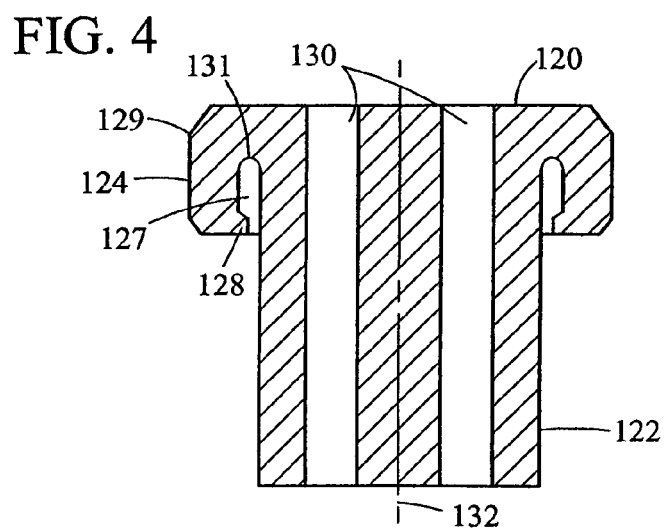
FIG. 4 is a cross-sectional view of an exemplary seal taken along lines 4—4 of FIG. 3.

Referring now to FIG. 4, the seal channels 130 extend from the upper portion 120 through the lower portion 122 and exit through the seal bottom 126. Flange 124 extends outward from the upper portion 120 and along lower portion 122 creating a bend 129. The bottom of flange 124 tapers inward towards the seal 140 such that a protrusion or tip 128 can contact the upper shield 20 when the seal 40 is installed therein (as shown in FIG. 2).

The seal 40 and flange 124 preferably have a geometry and size complementary with the shield upper portion 22. Essentially, the seal 40 should, once crimped, establish a fluid tight seal between the seal 40 and the upper portion 22 of the upper shield 20 and between the seal 40 and the cables 64, 65. To further establish and maintain this fluid tight connection, the flange 124 is preferably designed such that the opening between bend 129 (and/or the protrusion) and the seal lower portion 122 is less than the thickness of shield upper portion 22 to be disposed between the bend 129 and the seal lower portion 122. As a result, the design specifications of the flange 124 are based upon obtaining the desired sealing between the flange 124 and the shield upper portion 22. Although many flange designs can be employed, such as a snap connection or the like, the flange 124 preferably comprises an upper portion, e.g., extension 131, disposed at or near the upper seal upper portion 120 which extends substantially perpendicularly from the seal 40 (e.g., angles of up to about 135° or so from the seal central axis 132 can be employed, with angles of about 30° to about 90° are preferred, and an angle of about 75° to about 90° more preferred). From extension 131, a bend 129 extends along lower portion 122 to form a recess 127 for receiving the shield upper portion 22. The angle at which the bend 129 extends from extension 131 can be any angle less than parallel with extension 131, with angles up to about 90° preferred. Depending upon the chosen angles for extension 131 and bend 129, a protrusion 128 can extend from bend 129 toward seal lower portion 122 to form a recess 127 having a opening width which is preferably up to the thickness of the shield upper portion 22 which will be received therein, and which is more preferably smaller than the shield upper portion 22 thickness so as to form a fluid tight seal between the flange 124 and the shield upper portion 22. This design enables the flange 124, to both provide a secure fitting with the upper shield 20 and to create a secondary sealing point. During sensor operation, high temperatures can cause the seal to outgas or otherwise shrink. The shrinkage draws the flange 124 closer toward the upper shield 20, thereby forming a tighter seal. Consequently, unlike conventional seals that require a two piece systems (e.g., seal and boot) to compensate for shrinkage during operation, the present seal naturally compensates for operating shrinkages. To further ensure fluid tight sealing, flange 124 is preferably disposed, continuously and concentrically around the seal body. Alternatively, if fluid tight sealing of the flange is not required, the flange 124 can be disposed intermittently around the seal body.

Figure 5:
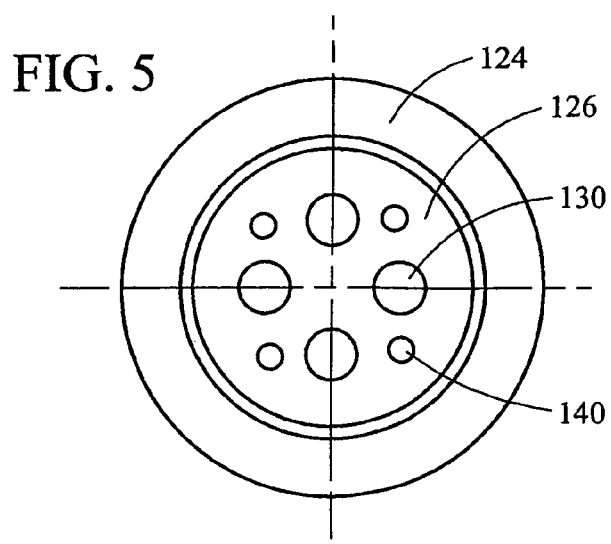
FIG. 5 is an isometric bottom view of an exemplary seal.

Now referring to FIG. 5, one embodiment of the bottom view of the one-piece multifunctional seal 40 is illustrated. At the bottom 126 of the seal 40 is the other end of the channels 130 (note, four channels are shown, but any number can be employed based upon the desired number of cables and connections; typically about 3 to about 8 cables (and channels) are employed). Also disposed on the bottom 126 are optional projections 140. The projections 140 are designed to contact the terminal support 60 (as shown in FIG. 2), thereby holding the terminal support 60 in the desired location within the upper shield 20 and dampening vibrations or shock loads that can have an impact on the sensor. The projections 140 act similar to a spring, absorbing the vibrations and thereby extending the sensor life by reducing stress and other loads, while minimizing contact between the seal 40 and the terminal support 60. The projections 140, which can be employed in any quantity, are preferably spaced equidistant from each other to provide equal distribution of stresses associated with shock and vibrations. These projections 140 are also preferably designed to form a sufficient air gap between the seal 40 and the terminal support 60 to substantially insulate the seal 40 from convective heat transfer from the terminal support 60. Basically due to the minimal physical contact between the terminal support 60 and the seal 40, the transfer of heat from the lower components of the sensor to the seal 40 is decreased.

Unlike conventional seals that either leak before 500 hours of thermal cycling between about −40° C. and 200° C. due to out-gassing shrinkage or that require a second sealing component (e.g., a boot), the present seal maintains fluid tight sealing after the same thermal cycling for greater than about 750 hours, and even for over about 1,000 hours. Furthermore, under additional testing, with the engine operating at about 1,000° C. (e.g., the sensor seal being exposed to temperatures of about 250° C.), the present seal has maintained fluid tight sealing for about 250 hours, with at least about 1,000 hours anticipated.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

We claim:

1. A gas sensor, comprising:
 a sensing element having a lower portion disposed within a subassembly and an upper portion disposed within a wiring harness assembly comprising an upper shield disposed around a wiring harness; and
 a one-piece seal having a body disposed in a first portion of said upper shield, and a flange, wherein said flange comprises an extension which protrudes from said one-piece seal over an edge of said upper shield, with a bend which extends from said extension along said upper shield toward said subassembly.

2. The gas sensor of claim 1, wherein said subassembly further comprises: a shell disposed around said lower portion of said sensing element; an upper insulator, wherein at least a portion of said upper insulator is disposed between said sensing element and said shell; and a lower shield disposed around an end of said sensing element, said lower shield in physical communication contact with said shell, and having a plurality of apertures.

3. The gas sensor of claim 1, wherein said one-piece seal comprises a material selected from the group consisting of fluorelastomer, silicone, rubber, perfluoroelastomer, and combinations comprising at least one of the foregoing materials.

4. The gas sensor of claim 1, wherein said flange further comprises a protrusion which extends from said bend toward said upper shield, wherein a distance between said protrusion and said body is about equal to or less than a thickness of said upper shield.

5. The gas sensor of claim 4, further comprising a fluid tight seal between said protrusion and said upper shield.

6. The gas sensor of claim 1, wherein said one-piece seal further comprises a lower surface and at least one projection protruding from said lower surface toward said subassembly.

7. A method for producing a gas sensor, comprising:
 disposing an upper portion of a sensing element within a wiring harness assembly comprising an upper shield disposed around a wiring harness;
 disposing a lower portion of said sensing element within a subassembly;
 disposing at least a portion of a body of a one-piece seal concentrically with a first portion of said upper shield, and a portion of a flange of said one-piece seal over an edge of said upper shield, wherein said flange further comprises an extension which protrudes from said seal over said edge of said upper shield, with a bend which extends from said extension along said upper shield toward said subassembly; and
 crimping said upper shield around said body of said one-piece seal.

8. The method as in claim 7, further comprising forming a fluid tight seal between said protrusion and said upper shield.

9. A gas sensor, comprising:
 an upper shield and a lower shield, with a sensing element having a lower portion disposed within the lower shield; and
 a one-piece seal disposed into the upper shield, the seal comprising
  a body;
  an upper portion having a flange, said flange having an extension which protrudes from said upper portion, a bend which extends from said extension along said body, and a protrusion which extends from said bend toward said body; and
  at least one channel extending through said body from said upper portion to a lower surface.

10. The gas sensor as in claim 9, further comprising at least one projection protruding out of said lower surface.

11. The gas sensor as in claim 9, further comprising a material selected from the group consisting of fluorelastomer, silicone, rubber, perfluorelastomer, and combinations comprising at least one of the foregoing materials.

12. A gas sensor, comprising:
 a sensing element, having a lower portion disposed within a subassembly and an upper portion disposed within a wiring harness assembly comprising an upper shield disposed around a wiring harness; and
 a one-piece seal having a body disposed in a first portion of said upper shield, a flange, a lower surface, and at least one projection protruding from said lower surface toward said subassembly, wherein an edge of said upper shield is disposed between at least a portion of said flange and said body.

13. The gas sensor of claim 12, wherein said subassembly further comprises: a shell disposed around said lower portion of said sensing element; an upper insulator, wherein at least a portion of said upper insulator is disposed between said sensing element and said shell; and a lower shield disposed around an end of said sensing element, said lower shield in physical communication with said shell, and having a plurality of apertures.

14. The gas sensor of claim 12, wherein said one-piece seal comprises a material selected from the group consisting of fluorelastomer, silicone, rubber, perfluoroelastomer, and combinations comprising at least one of the foregoing materials.

15. A gas sensor, comprising:
 a sensing element having a lower portion disposed within a subassembly and an upper portion disposed within a wiring harness assembly comprising an upper shield disposed around a wiring harness; and
 a seal comprising
  a body disposed in physical communication with an inner wall of a first portion of said upper shield to form a primary sealing point, and
  a flange disposed in physical communication with an edge of said upper shield such that said edge is disposed between at least a portion of said flange and said body, wherein said flange is capable of shrinking around said edge during operation of said gas sensor to form a secondary sealing point.

16. The gas sensor of claim 15, wherein said seal is a one-piece seal.

17. The gas sensor of claim 15, wherein said flange comprises an extension which protrudes from said one-piece seal over said edge of said upper shield, with a bend which extends from said extension along said upper shield toward said subassembly.

18. The gas sensor of claim 15, wherein said one-piece seal is a moldable one-piece seal made of a material capable of withstanding temperatures commensurate with operation of an engine.

19. The gas sensor of claim 18, wherein said moldable one-piece seal comprises a material selected from the group consisting of fluorelastomer, silicone, rubber, perfluoroelastomer, and combinations comprising at least one of the foregoing materials.

20. The gas sensor of claim 15, wherein said flange is continuously and concentrically disposed around said body.

21. The gas sensor of claim 15, wherein said flange is disposed intermittently around said body.

* * * * *